(12) United States Patent
Danchisin et al.

(10) Patent No.: US 9,566,117 B2
(45) Date of Patent: Feb. 14, 2017

(54) PROPHYLACTIC KIT APPARATUS

(75) Inventors: Jennifer E. Danchisin, Downers Grove, IL (US); Tom Gregory, Sr., Cedarburg, WI (US); Steve Henrikson, Morristown, TN (US); Deborah Adler, New York, NY (US)

(73) Assignee: Medline Industries, Inc., Northfield, IL (US)

( * ) Notice: Subject to any disclaimer, the term of this patent is extended or adjusted under 35 U.S.C. 154(b) by 0 days.

(21) Appl. No.: 14/237,719

(22) PCT Filed: Aug. 8, 2012

(86) PCT No.: PCT/US2012/049984
§ 371 (c)(1),
(2), (4) Date: Oct. 29, 2014

(87) PCT Pub. No.: WO2013/022964
PCT Pub. Date: Feb. 14, 2013

(65) Prior Publication Data
US 2015/0050627 A1    Feb. 19, 2015

Related U.S. Application Data

(63) Continuation-in-part of application No. 13/206,289, filed on Aug. 9, 2011, now Pat. No. 8,875,940.

(51) Int. Cl.
*A61J 1/00*    (2006.01)
*A61B 19/02*    (2006.01)
(Continued)

(52) U.S. Cl.
CPC ............. *A61B 19/026* (2013.01); *A61B 50/30* (2016.02); *A61J 1/00* (2013.01); *A61J 7/0076* (2013.01);
(Continued)

(58) Field of Classification Search
CPC ............. A61J 1/00; A61K 8/38; A61B 19/026
(Continued)

(56) References Cited

U.S. PATENT DOCUMENTS 2,391,094 A    12/1945    Karg
3,450,308 A    6/1969    Schoenefeld
(Continued)

FOREIGN PATENT DOCUMENTS

EP    2082963    7/2009
EP    2532342    12/2012
(Continued)

OTHER PUBLICATIONS

Extended European Search Report from European Patent Application No. 12821743.7-1651 Dated Mar. 16, 2015.
(Continued)

*Primary Examiner* — Patrick Mackey
(74) *Attorney, Agent, or Firm* — Fitch, Even, Tabin & Flannery LLP

(57) ABSTRACT

A prophylactic kit apparatus configured to be used with only a single patient includes a plurality of sealed modules and a housing configured to contain those sealed modules such that only one of the plurality of sealed modules can be removed from the housing at a time. This kit may include a physically-discrete informational patient aid disposed within the housing and having information disposed thereon. By one approach these physically-discrete informational patient aids can have a bookmark form factor. So configured, a medical services provider can readily provide the physically-discrete informational patient aid to a patient to thereby facilitate the patient becoming informed regarding the corresponding prophylactic service with little or no burden on the service provider.

8 Claims, 5 Drawing Sheets

(51) Int. Cl.
  *A61K 8/66* (2006.01)
  *A61K 8/365* (2006.01)
  *A61Q 11/00* (2006.01)
  *A61J 7/00* (2006.01)
  *A61J 7/04* (2006.01)
  *A61K 8/38* (2006.01)
  *B65D 83/00* (2006.01)
  *G09B 19/00* (2006.01)
  *A61J 1/03* (2006.01)

(52) U.S. Cl.
  CPC ............... *A61J 7/0084* (2013.01); *A61J 7/04* (2013.01); *A61K 8/365* (2013.01); *A61K 8/38* (2013.01); *A61K 8/66* (2013.01); *A61Q 11/00* (2013.01); *B65D 83/00* (2013.01); *G09B 19/00* (2013.01); *A61B 2050/3005* (2016.02); *A61J 1/035* (2013.01); *A61K 2800/884* (2013.01)

(58) Field of Classification Search
  USPC ................. 221/3, 12, 97, 99, 102, 303
  See application file for complete search history.

(56) References Cited

U.S. PATENT DOCUMENTS

| | | |
|---|---|---|
| 4,382,526 A | 5/1983 | Stone |
| 5,221,024 A | 6/1993 | Campbell |
| 5,244,096 A | 9/1993 | Stoner |
| 2004/0091432 A1 | 5/2004 | Dulin |
| 2008/0000798 A1 | 1/2008 | Gutmann et al. |

FOREIGN PATENT DOCUMENTS

| | | |
|---|---|---|
| GB | 2122578 | 1/1984 |
| WO | 0061444 | 10/2000 |
| WO | 03062091 A1 | 7/2003 |

OTHER PUBLICATIONS

Article 94(3) EPC from European Patent Application No. 12821743.7 dated Aug. 30, 2016.
International Search Report issued Feb. 19, 2013 in PCT/US2012/049984.

PROPHYLACTIC KIT APPARATUS

RELATED APPLICATION(S)

This application is a continuation-in-part of and claims benefit to U.S. patent application Ser. No. 13/206,289, entitled Prophylactic Kit Apparatus and filed Aug. 9, 2011, which is incorporated by reference in its entirety herein.

TECHNICAL FIELD

This invention relates generally to prophylactic kits for preventing or at least mitigating the worsening of physical impairments and more particularly to preventing or at least mitigating the worsening of disease processes.

BACKGROUND

Various medical therapies serve to reverse, halt, or at least aid in controlling symptoms that pertain to corresponding physical maladies. Prophylactic approaches, on the other hand, while possibly having one or more therapeutic qualities in some cases, primarily serve to prevent (completely or at least to a large extent) a corresponding physical malady.

Ventilator-associated pneumonia (VAP) is one example of a physical malady that receives considerable attention as the National HealthCare Safety Network identified VAP as being the second most common hospital-acquired infection and one that is deadlier than either central line-associated bloodstream infections or sepsis. In response, various organizations have identified prophylactic regimens that offer a demonstrable ability to prevent VAP.

Such prophylactic regimens make use of a variety of prophylactic agents that require relatively frequent and periodic administration to the patient. These regimens are sufficiently complex that administration compliance issues can and do arise. The applicant has determined that existing approaches in these regards leave room for considerable improvement. This includes facilitating the provision of information to the patient themselves regarding the nature of the prophylactic process itself and the maladies against which the prophylactic process serves.

BRIEF DESCRIPTION OF THE DRAWINGS

The above needs are at least partially met through provision of the prophylactic kit apparatus having a physically-discrete informational patient aid described in the following detailed description, particularly when studied in conjunction with the drawings, wherein.

Figure 1:
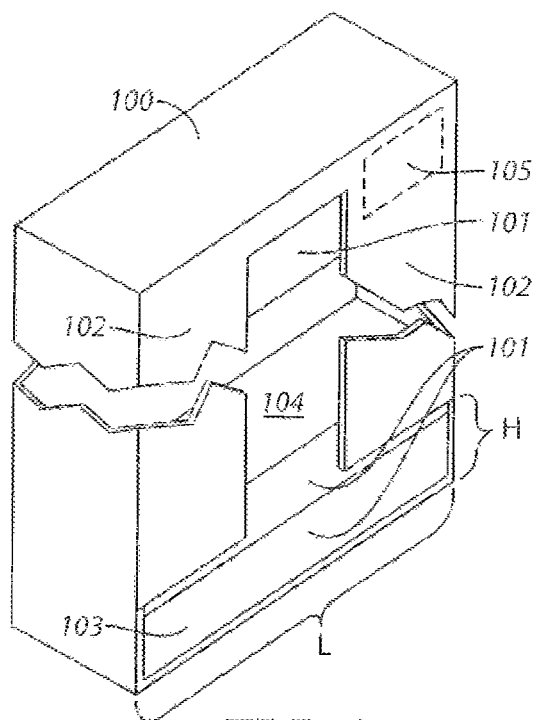
FIG. 1 comprises a perspective view as configured in accordance with various embodiments of the invention.

Common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments comprise a prophylactic kit apparatus configured to be used with only a single patient. This kit includes a plurality of sealed modules and a housing configured to contain those sealed modules such that only one of the plurality of sealed modules can be removed from the housing at a time. This kit may also include a physically-discrete informational patient aid disposed within the housing and having information disposed thereon. By one approach the physically-discrete informational patient aid can have a bookmark form factor. So configured, a medical services provider can readily provide the physically-discrete informational patient aid to a patient to thereby facilitate the patient becoming informed regarding the corresponding prophylactic service.

By one approach, the sealed modules are to be used in a particular order and the housing is further configured to facilitate the removal of the sealed modules in only that particular order. In such a case, and as desired, the physically-discrete informational patient aid can be disposed between a first one of the sealed modules that is to be removed from the housing at a time of initially servicing the patient and a next adjacent one of the sealed modules. In any event the physically-discrete informational patient aid can be loosely disposed within the housing with respect to the sealed modules or can be removably attached to one of the sealed modules.

By one approach the plurality of sealed modules are stacked vertically within the housing when the housing is oriented in a dispensing orientation. To facilitate dispensing only one sealed module at a time the housing can include a dispensing slot that is sized to accommodate at least one of the sealed modules but not two or more.

These teachings are highly flexible and scalable in practice and can serve to greatly leverage a wide variety of existing prophylactic agents, regimens, and protocols. Such a prophylactic kit apparatus can also greatly facilitate prompting and ensuring compliance with respect to proper and timely administration of any number of prophylactic regimens.

These and other benefits may become clearer upon making a thorough review and study of the following detailed description. Referring now to the drawings, various illustrative prophylactic kit apparatuses that are compatible with many of these teachings will be presented.

FIG. 1 illustrates a prophylactic kit apparatus configured to be used with only a single patient. That is, such a kit will be assigned to only a single patient and the contents of this kit are not presumed to be shared with other persons. The examples provided herein also presume that this kit is configured to be used for no longer than a predetermined period of time (such as, for example, one twenty-four hour day). Accordingly, one provides additional such kits to the patient if and as the need for prophylactic attention persists for subsequent like periods of time.

This kit includes a housing 100 configured to contain a plurality of sealed modules 101. Various of the figures (including FIG. 1) depict this housing 100 oriented in a dispensing orientation. So oriented, the sealed modules 101 are stacked vertically within the housing 100. Pursuant to one approach these sealed modules 101 are loosely contained within the housing prior to removal from the housing 100 (in that none of the sealed modules 101 are physically connected to another of the sealed modules 101). Pursuant to these teachings this housing 100 is configured to contain these sealed modules 101 such that only one of the plurality of sealed modules 101 can be removed from the housing at a time.

In this illustrative example the sidewalls, back, top, and bottom panels of the housing 100 are closed. These teachings will, however, accommodate including small apertures through these surfaces if desired provided those apertures are not sufficiently large to accommodate removal of one of the sealed modules 101 from within the housing 100. The front panel of the housing 100 includes a dispensing slot 103 (located at the bottom of the front panel) sized to accommodate only one of the sealed modules 101 at a time.

Accordingly, this dispensing slot 103 can be larger than a single one of the sealed modules 101 so long as the dispensing slot 103 cannot simultaneously accommodate two or more of the sealed modules 101. In particular, this dispensing slot 103 has a height H and a length L that will readily permit one, but not two or more, of the sealed modules 101 therethrough. So configured, only one of the sealed modules 101 can be removed from the housing 100 at a time.

In this illustrative example the front panel of the housing 100 also includes a window 104 defined, in part, by side window panels 102. This window 104 is of insufficient dimensions to permit the sealed modules 101 to readily pass therethrough. So configured (and as described below in more detail) this window 104 permits an observer to view at least many of the sealed modules 101 and thereby glean considerable information regarding, for example, the contents of those sealed modules 101. If desired, a sheet of clear plastic or the like can optionally be placed within this window 104.

In at least some cases the contents of these various sealed modules 101 are to be used in a particular order of service for the patient and pursuant to a particular periodicity. For example, use of many of the sealed modules 101 may presume sequential use while observing four-hour periodicity. Disposing these sealed modules 101 within such a housing 100 will permit only one such sealed module 101 to be removed from the housing 100 at a time and in the particular order in which the sealed modules 101 are stacked within the housing 100 to thereby help assure that medical service providers employ only appropriate sealed modules 101 at a time of service.

If desired, these teachings optionally permit including an electronic timer 105 with the kit. This electronic timer 105 can be disposed, for example, on the front panel of the housing 100. Such a timer can serve to facilitate timely administration of the sealed modules 101 in service of the patient. This can comprise, by one approach, providing an appropriate alarm (audible, visual, haptic, wireless, or any combination of the foregoing) to alert a medical service provider of a need to now dispense the next sealed module 101 and utilize the prophylactic contents of that sealed module 101 for the corresponding patient. By another approach, in lieu of the foregoing or in combination therewith, this can comprise providing a real-time display and/or a count-up or count-down display to help an observer calculate or otherwise understand when a next treatment event becomes due.

Such a housing 100 can be comprised of any suitable material. This can include, for example, paperboard materials (including cardboard, corrugated cardboard, Bristol board, and so forth), plastic materials, metals, and combinations of the foregoing. By one approach this housing 100 comprises a one-time-use housing. These teachings will also accommodate, however, providing a reusable housing into which one can repeatedly insert the aforementioned sealed modules 101 at a time of need.

Figure 2:
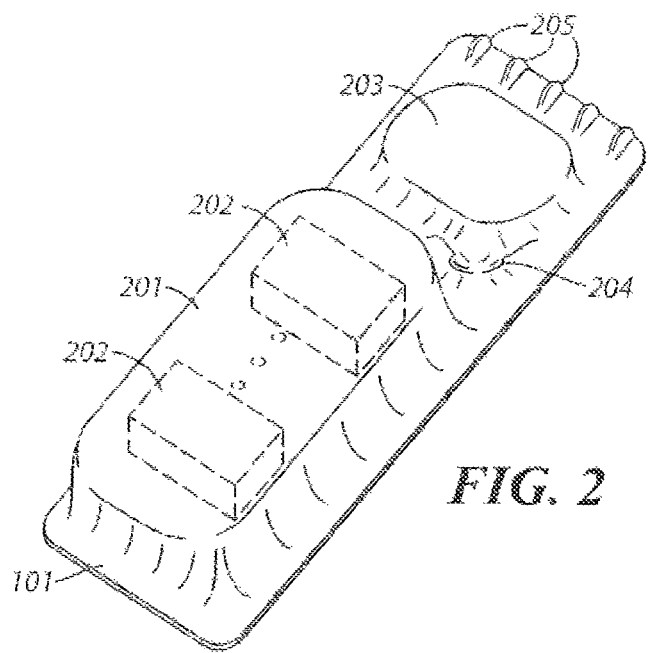
FIG. 2 comprises a perspective view as configured in accordance with various embodiments of the invention.
Figure 3:
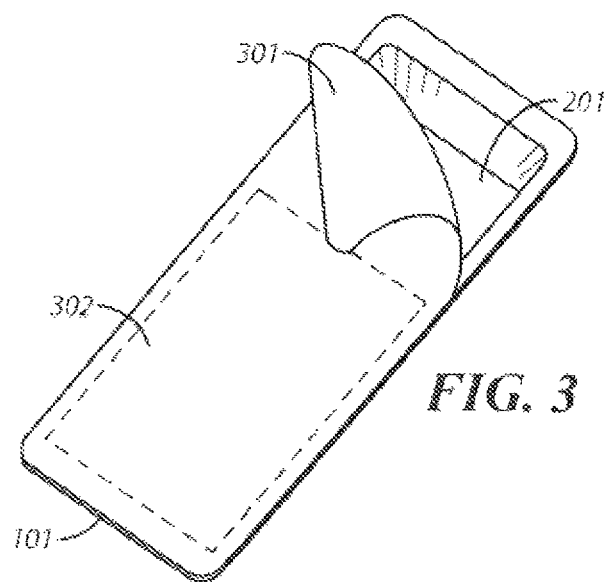
FIG. 3 comprises a perspective view as configured in accordance with various embodiments of the invention.

Referring to FIGS. 2 and 3, the aforementioned sealed modules 101 can comprise one or more sealed containers 201 that each contain at least one prophylactic agent 202 to be used in service of the corresponding patient. In some cases each sealed module 101 in a given housing 100 may contain the same prophylactic agent(s) 202. In other cases, however, the prophylactic agents 202 may vary, at least to some extent, from one sealed module 101 to the next.

Consider, for example, that when the kit serves to prevent ventilator-associated pneumonia the prophylactic agents may comprise a set-up kit (including, for example, a yankauer, a suction-tubing "Y" connector, and a separate turn-valve (such as a suction handle) to control suction administration), oral-cleaning instruments (including, for example, suction toothbrushes (with or without integrated tongue and gum-cleaning pads), moisturizing gels and applicator swabs, graduated catheters for subglottal suctioning, and dentifrice-treated suction swabs), and mouthwashes (such as, for example, the prescription chlorhexidine gluconate 0.12% oral rinse, saliva enzyme-based mouthwash (such as, but not limited to, Biotine), or hydrogen peroxide to note a few examples in these regards).

In such a case, a VAP-prevention kit may comprise a housing 100 that includes three different sealed modules 101—an initial set-up module that provides a yankauer to be used with other prophylactic agents from other sealed modules 101 and useful mechanisms to facilitate attaching the yankauer to a suction system and controlling that suction; suction swab modules; and suction toothbrush and catheter modules. These various sealed modules 101 are stacked within the housing 100 in their intended order of usage and with the first-used sealed modules at the bottom of that stack as those will be the first sealed modules 101 to dispense from the housing 100.

The above-described portions of the sealed module 101 can comprise a waterproof material such as a rigid or semi-rigid plastic of choice. The selected material can be clear and substantially transparent, if desired, to permit the prophylactic agent(s) 202 contained therein to be externally viewed. These teachings will also accommodate, however, using colored or otherwise opaque or largely opaque material if desired.

By one approach, some or all of the sealed modules 101 can include containers 203 that do not include (when sealed) a prophylactic agent or any other contents (aside from atmospheric contents of choice). Such a container 203 can serve instead as a well to receive, for example, a prophylactic liquid such as a mouthwash. In particular, at a time of use, a mouthwash container can be opened and all or a portion of its contents poured into such a well to facilitate the use of that liquid by the medical services provider.

As shown particularly in FIG. 2 some or all of the sealed modules 101 can include a physical user interface 204 to facilitate permitting a user to select and remove a single one of the sealed modules 101 via the above-described dispensing slot 103 of the housing 100. In the illustrated example, this physical user interface 204 comprises a small well shaped to receive and suitably interact with a user's thumb.

If desired, corrugations 205 can be included to impart strength and rigidity to the sealed module 101 where desired.

As shown in FIG. 3, by one approach a paper or paper-like cover 301 can cover the various containers 201 of the sealed module 101 to thereby seal those container areas. An adhesive of choice can be employed for this purpose. This seal can be hermetic if desired. In any event, so configured, this cover 301 can be readily removed at a time of need by simply peeling the cover 301 away from the remaining portion of the sealed module 101 to thereby expose the containers and permit access to the prophylactic agents 202 stored therein.

By one approach this cover 301 can have information 302 printed (or otherwise placed) thereon. As one example in these regards, this information 302 can comprise administration-facilitation instructional content regarding proper administration of the prophylactic agent(s) 202 contained in this particular sealed module 101. Such instructional content can comprise, for example, explanatory and/or cautionary text, icons, color coding, and graphic content in these regards. The graphic content, for example, can comprise a numbered sequence of images that offer step-by-step illustrative examples regarding how to set up the prophylactic agent(s) for use and then use those materials for the benefit of the patient.

As noted above, the prophylactic agents included in a given kit can include one or more prescription drugs such as, but certainly not limited to, a prescription-strength oral rinse comprising chlorhexidine gluconate 0.12%. In some regulated jurisdictions it may be impermissible to include such a prescription-grade agent within the aforementioned sealed modules 101. By one approach, the sealed module 101 can instead include an external nesting area 401 as illustrated by way of example in FIG. 4.

This external nesting area 401 can be configured to receive the container 402 for the prophylactic agent in question. This can comprise either loosely receiving that container 402 or configuring the sealed module 101 to mate with the container 402 using, for example, a snap fit. If desired, a sheet 403 of tearable or otherwise removable paper, plastic, or the like can be partially disposed over the container 402 and adhered to the sealed module 101 in order to further contain the container 402 and/or provide a further cautionary note to the observer regarding the removal and use of the contents of that container 402.

Figure 5:
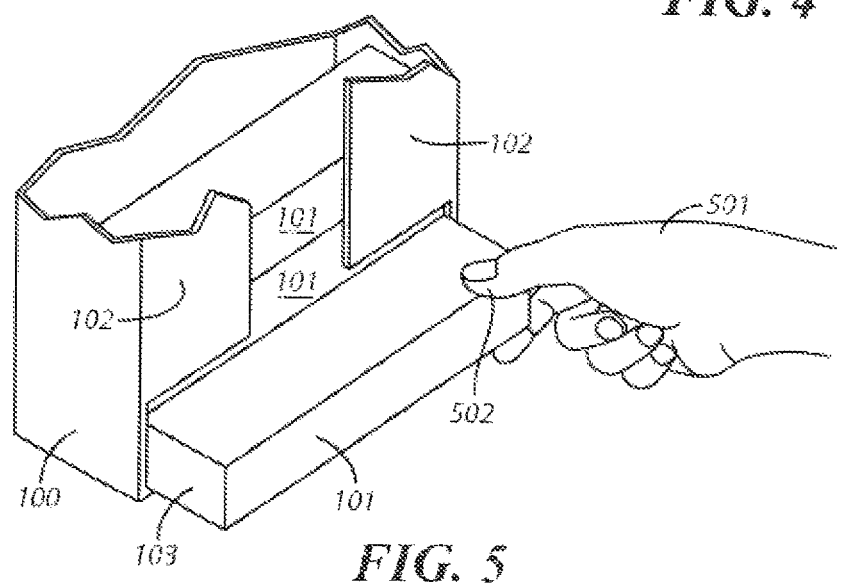
FIG. 5 comprises a perspective partial view as configured in accordance with various embodiments of the invention.

As mentioned above, these teachings provide for configuring a sealed-module housing that permits only one sealed module to be dispensed at a time, and in a particular order as well. FIG. 5 illustrates how a dispensing slot 103, working in combination with the aforementioned window side panels 102, permits a single sealed module 101 to be gripped by a user 501 (using, for example, a thumb 502) and easily removed from the housing 100 via that dispensing slot 103. Upon removing that lowermost sealed module 101, of course, the remaining sealed modules 101 within the housing 100 will drop down to thereby permit the next-in-order sealed module 101 to be similarly dispensed at the appropriate time. If desired, a biasing member such as one or more springs (not shown) can be located within the housing 100 and above the sealed modules 101 to urge the sealed modules 101 towards the dispensing slot 103.

Figure 6:
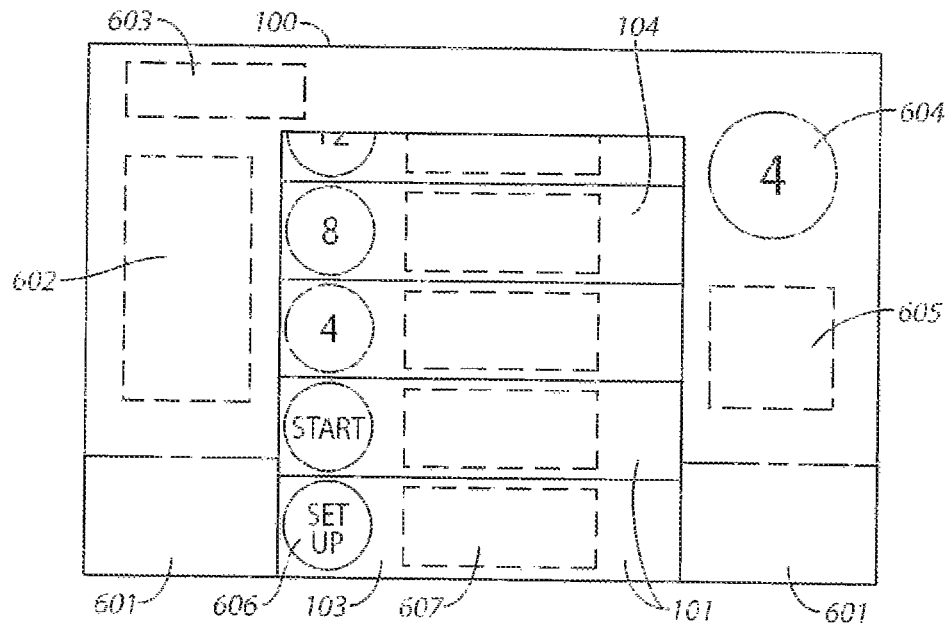
FIG. 6 comprises a front-elevational view as configured in accordance with various embodiments of the invention.

If desired, and referring now to FIG. 6, the dispensing slot 103 can be partially (or even fully, if desired) blocked by one or more tear-away flaps 601. These tear-away flaps 601 can be defined, at least in part, by scored or perforated lines to permit the tear-away flaps 601 to be readily separated from the housing 100 to thereby fully expose and define the dispensing slot 103.

If desired, one or more exterior surfaces of the housing 100 can have instructional and/or cautionary content disposed thereon. For example, and only by way of illustration, a first area 602 can present compliance-facilitation content. This can of course include information regarding the correct use and timing of use of the contents of the kit. This content can also refer to specifics that relate to the overall regimen including specifics that do not pertain, at least directly, to the prophylactic agents contained in the kit. For example, when the kit serves to prevent the occurrence of ventilator-associated pneumonia, this information can include other related compliance specifics such as maintaining the patient's head of their bed between thirty degrees and forty-five degrees and interrupting the patient's state of sedation on a daily basis.

As noted above, such a kit may be configured and intended for use during only a predetermined period of time such as twenty-four consecutive hours. In such a case, and again by way of illustration rather than limitation, another area 603 on the exterior surface of the housing 100 can include information regarding this predetermined period of time. For example, when the kit comprises a kit of prophylactic agents intended and designed for use over a single twenty-four hour period, this information can include the words "24 HR SYSTEM" or the like.

Also as noted above, a given kit can be configured and designed for at least some of its constituent sealed modules 101 to be administered at even periodic intervals, such as every four hours. In such a case, and again only by way of an illustrative example, yet another portion 604 of the housing's exterior can include information in these regards.

And yet another portion 605 of the housing's exterior can contain information that details the contents of the kit. For a ventilator-associated pneumonia prevention kit, for example, this might identify a single set-up kit, two suction toothbrush and catheter modules, and four suction swab modules.

It will be understood that such informational content can be located elsewhere on the housing 100 and/or that the external surfaces of the housing 100 can include other kinds of information as desired. As one example in these regards, the relatively large area offered on the backside of the housing 100 can include pictures or other illustrations (along with corresponding text) to generally (or specifically) depict and describe how to set up a suction canister to operate with the various kit components.

The aforementioned window 104 (as well as the dispensing slot 103) permit an observer to view at least some of the stacked sealed modules 101 from their sides. As noted above, these sealed modules 101 can be stacked such that they are dispensed in an intended order of usage. In addition, if desired, at least some of the sealed modules can include a periodicity indicator 606. In the illustrative example shown, for example, the first sealed module is labeled "set up" and contains the items required to make appropriate use of the remaining packed items. The second sealed module is labeled "start" and includes the items that the medical service provider will first use when beginning the prophylactic regimen for a given patient. The third sealed module is labeled "4" to denote that this sealed module is to be used four hours later (presuming this kit to contain items that are to be administered periodically at four-hour intervals), and so forth.

In addition to the foregoing or in lieu thereof, some or all of the sealed containers can also include a module title and/or contents list 607 that is similarly viewable via the dispensing slot 103 and/or the window 104.

These teachings will also accommodate making use of color coding as desired. By one approach, for example, color coding can be applied to some or all of the sealed modules 101. This might comprise, for example, using a dark blue color to indicate sealed modules 101 that contain set-up materials and another color or colors for the remaining sealed modules 101.

Kits for ventilator-associated pneumonia prevention can include any of a variety of mouthwashes. By one approach, color coding can serve to indicate which mouthwash one will find in each such kit. As an illustrative example in these regards, the color gold can identify sealed modules (other than start-up kit sealed modules) that are used in a kit that contains a chlorhexidine gluconate 0.12% oral rinse while light blue identifies sealed modules 101 for kits that utilize a saliva enzyme-based mouthwash and green identifies sealed modules 101 for kits that contain hydrogen peroxide-based mouthwashes.

Using this approach, at least some sealed modules that are color coded in a given housing 100 will all share a same color coding based on a particular type or selection of prophylactic agent (such as mouthwash) regardless of whether each color-coded sealed module 101 actually contains the particular prophylactic agent that determines the color coding. This approach can aid in presenting an easily understood color-coded presentation that effectively communicates the desired information to the observer.

Figure 4:
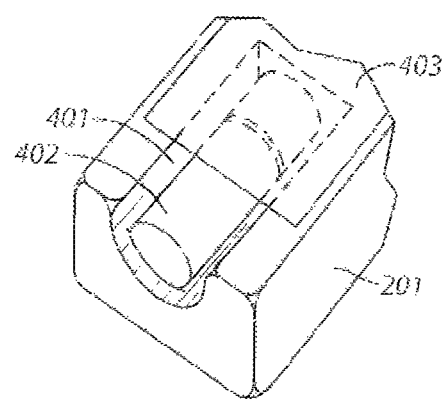
FIG. 4 comprises a perspective partial view as configured in accordance with various embodiments of the invention.
Figure 7:
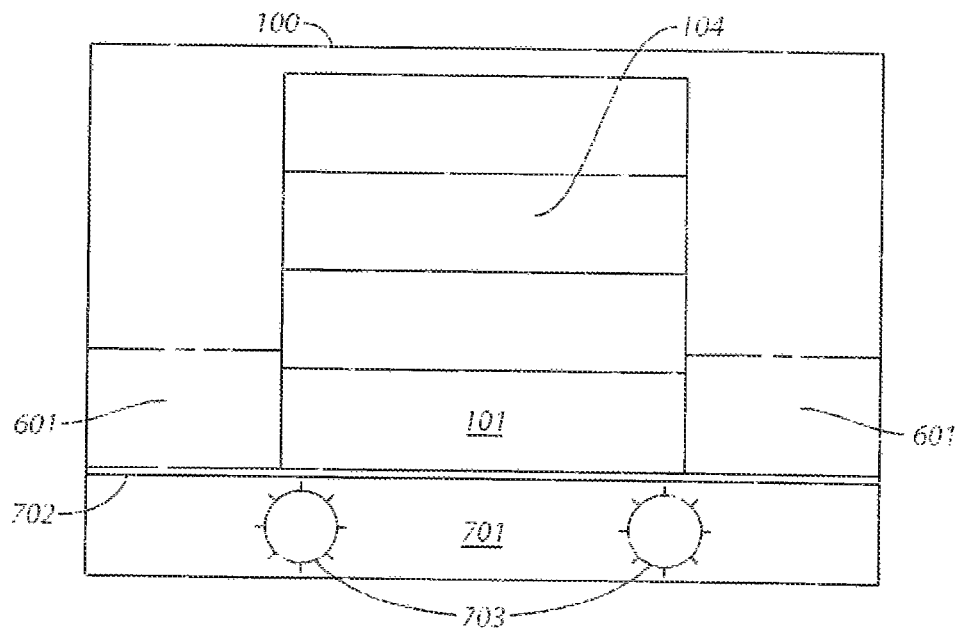
FIG. 7 comprises a front-elevational view as configured in accordance with various embodiments of the invention.

As mentioned above, in some cases it may be undesired to place a particular item, such as a prescription-grade prophylactic agent, within a sealed module as described. FIG. 4 described above illustrates one way to associate such an agent with a given sealed module 101 by securing the agent to the exterior of the sealed module 101. FIG. 7 illustrates another approach in these same regards.

In particular, FIG. 7 illustrates that the housing 100 can include a discrete storage area 701 to separately store such things as prescription-grade prophylactic agents. In this particular example a shelf 702 serves to separate this storage area 701 from the remainder of the housing 701 and cavities 703 are formed through a front panel to receive and retain the agent until desired. As shown, these cavities 703 include scored segments around the periphery of the cavities 703 to help receive and captivate, for example, a bottle-shaped container.

Figure 8:
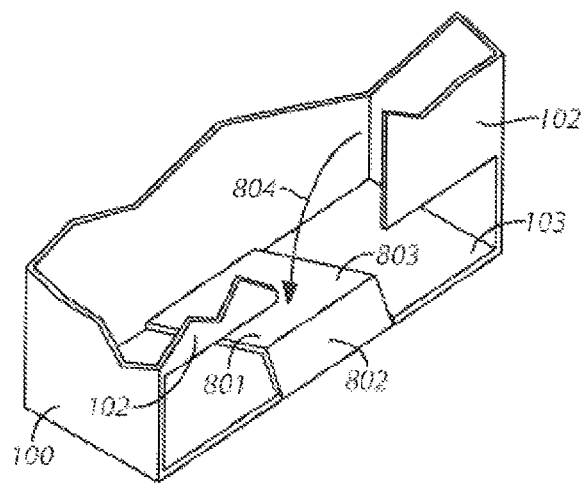
FIG. 8 comprises a perspective partial view as configured in accordance with various embodiments of the invention.

By one approach, and referring now to FIG. 8, the housing 100 can further include a ramp 801 to hold the sealed modules 101 at a non-horizontal dispensing angle. In particular, this ramp 801 is rearwardly inclined. This inclined orientation, in turn, will tend to permit gravity to bias the sealed modules 101 towards the rear of the housing 100 and thereby discourage inadvertent, non-aided dispensation of sealed modules 101 through the dispensing slot 103.

By one approach this ramp 801 can comprise a small front panel 802 and a sloping shelf 803 that forms an inclined surface to so orient and bias the sealed modules 101. In this example these two parts of the ramp 801 are integrally and contiguously comprised of the housing material itself. More particularly, at least a portion of the sloping shelf 803 is formed of the housing material that, when so removed, defines at least in part the aforementioned window 104 of the front panel of the housing 100. As suggested by the curved arrow denoted by reference numeral 804, this material can be pivoted rearwardly and downwardly (with respect to the small front panel 802) to thereby form the sloping shelf 803.

Such a housing can be operationally deployed in a variety of ways. By one approach the housing itself can simply be set upon a substantially horizontal surface such as a table top or shelf. By another approach the housing can be suspended from a suitable support apparatus (such as, but not limited to, a so-called IV pole, a wall-mounted hook or hooks, a bed frame, and so forth). To support suspending the housing 100 the housing 100 itself can optionally include a suspension interface.

Figure 9:
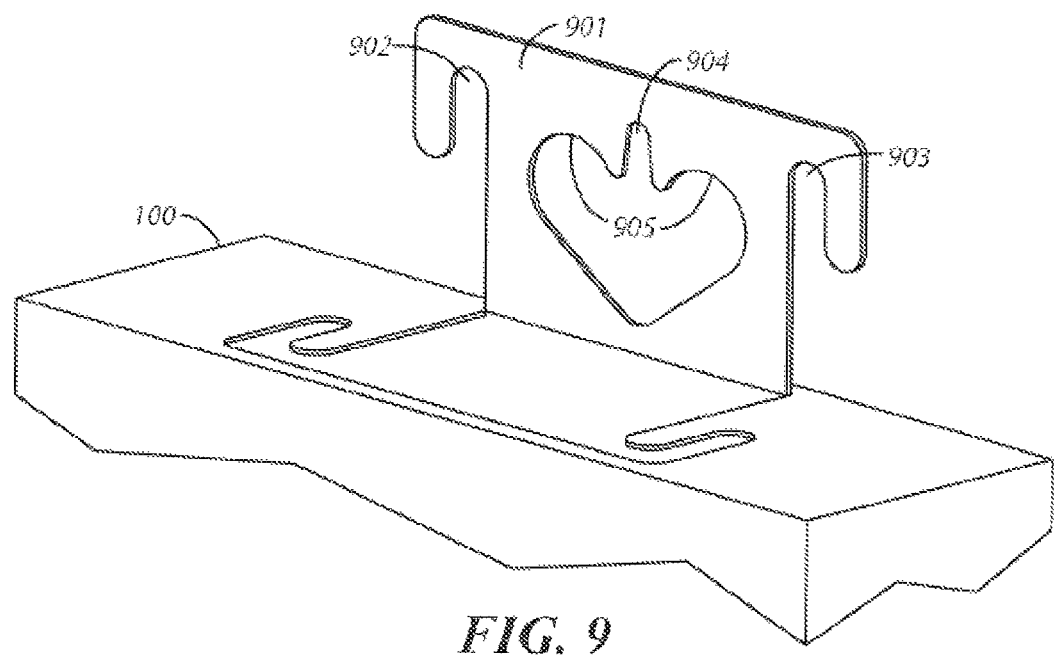
FIG. 9 comprises a perspective partial view as configured in accordance with various embodiments of the invention.

FIG. 9 provides one non-limiting example in these regards. In this example the suspension interface 901 comprises a flange that can be pivoted upwardly from the top of the housing 100 when and as needed. This suspension interface 901 includes a first pair of slots 902 and 903, a second pair of slots 905, and a single slot 904 to aid in accommodating a wide variety of support structures. The particular dimensions employed can be varied to suit the dimensions of possible support structures that the designer anticipates being available in the application setting.

These teachings are highly flexible in practice. As one example, the dimensions of the housing 100 can be varied as desired to suit as many sealed modules 101 as one may wish. As another example, these teachings can find useful application in a wide variety of application settings including bedside application settings, in surgery theaters, in first responder settings, in at-home settings, and so forth.

Such an approach is well suited to encouraging compliance with sometimes-complex prophylactic regimens that can span multiple shifts of caregivers and that pose changing requirements as to the specific treatment or task to be undertaken at any given time. Per these teachings, the medical service provider receives useful prompts regarding when to administer care to a given patient as well as unambiguous identification of which treatment to administer at that time.

Figure 10:
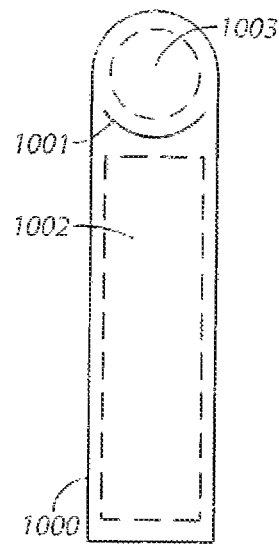
FIG. 10 comprises a top plan view as configured in accordance with various embodiments of the invention.

Referring now to FIG. 10, these teachings further contemplate optionally including a physically-discrete informational patient aid 1000 in such a housing 100. As used herein, the expression "physically-discrete" will be understood to refer to a physically separate and whole-unto-itself item. An ordinary battery, for example, comprises a physically-discrete item that does not lose its separate and whole nature upon merely being temporarily inserted into a battery-receiving receptacle in a battery-powered portable device.

Figure 11:
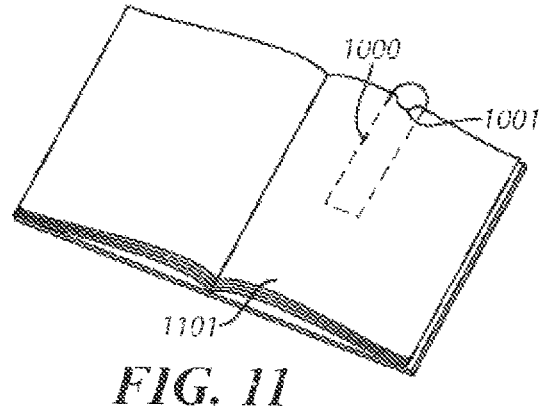
FIG. 11 comprises a perspective view as configured in accordance with various embodiments of the invention.

This physically-discrete informational patient aid 1000 can have, if desired, the form factor of a bookmark shown in the illustration provided at FIG. 10. By one approach this configuration can include an arcuate slot 1001 formed through the physically-discrete informational patient aid 1000 at one end thereof. Referring temporarily to FIG. 11, this arcuate slot 1001 can serve to temporarily capture the page of an item of reading material 1101 to thereby mark the reader's current point of progress. So configured, the physically-discrete informational patient aid 1000 can be easily placed as desired within the item of reading material 1101 and just as easily removed when desired.

Figure 12:
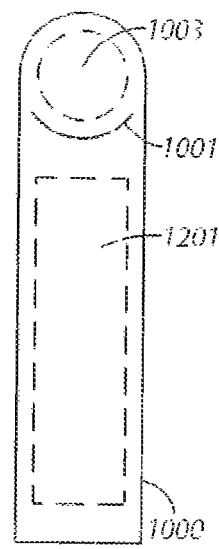
FIG. 12 comprises a bottom plan view as configured in accordance with various embodiments of the invention.

Referring again to FIG. 10, this physically-discrete informational patient aid 1000 has information 1002 disposed thereon. This information 1002 can comprise, for example, textual content regarding one, some, or all of: (1) an explanation of ventilator-associated pneumonia; (2) a description of at least some actions that reduce occurrences of ventilator-associated pneumonia; (3) a description of at least some actions the patient can personally take to reduce a likelihood of themselves contracting ventilator-associated pneumonia; and (4) an inspirational quotation. By one approach, and as shown in FIG. 12, the reverse side of the physically-discrete informational patient aid 1000 can also include such information 1201 as desired.

The form and/or type of the information can be directed to a particular intended audience. For example, by one approach the information can be of a form and type that anticipates an average adult's ability to comprehend. This can comprise, for example, a judicious choice and use of at least some explanatory words and/or concepts that an average high-school graduate (or higher) may be expected to know but that a minor might not be familiar with. By another approach, the information can be of a form and type that is suitable for a minor's comprehension (such as, for example, an average eight-year old's comprehension, an average thirteen-year old's comprehension, an average high-schooler's comprehension, and so forth as desired).

In any event, as one illustrative example in these regards the information 1002 on the front side of the physically-discrete informational patient aid 100 could read:

FOR PATIENTS AND THEIR FAMILIES UNDERSTANDING VAP
what you need to know . . .
WHAT IS VAP?
VAP means Ventilator-Associated Pneumonia. It's a lung infection a person gets when they're on a ventilator (breathing machine).
WHAT ARE HOSPITALS DOING TO PREVENT VAP?
Keeping the head of the bed elevated at 30-45 degrees if possible
Checking the patient's ability to breathe by himself or herself daily
Washing hands, using sanitizer and wearing gloves while providing care
Cleaning the patient's mouth and upper throat several times each day
Ensuring the ventilator and its parts are cleaned (or new parts are used) between patients
HOW CAN I HELP PREVENT VAP?
Wash and sanitize your own hands before and after touching the patient or ventilator.
Ask others, even doctors and nurses, to wash their hands.
Ask about raising the head of the bed.
Ask about how often the patient's mouth is cleaned and cared for.
Ask when the patient will be able to try breathing on his or her own.

The back side information 1201, in turn, could comprise an inspirational quote such as:

"Risk more than others think is safe. Care more than others think is wise. Dream more than others think is practical. Expect more than others think is possible."
Claude Bissell
or:

"From caring comes courage"
Lao Tzu

Other textual or image-based content can be included as desired. By one approach, for example, the front and/or back sides of the physically-discrete informational patient aid 1000 can include a graphic element (depicted schematically by the phantom-line circle denoted by reference numeral 1003) such as the image of a basket or bouquet of flowers, a cartoon character, a logo, or the image of a friendly medical services provider, to note but a few examples in these regards. The background field, in turn, can comprise essentially any color, design, or image that one might wish to employ. The front and back sides can be as similar or dissimilar in these regards as may be wished.

By one approach this physically-discrete informational patient aid 1000 can be loosely disposed essentially anywhere within the housing. By another approach the physically-discrete informational patient aid 1000 can be purposefully disposed within the housing 100 so as to be available when the medical service provider makes an initial use of the kit on behalf of a given patient.

Figure 13:
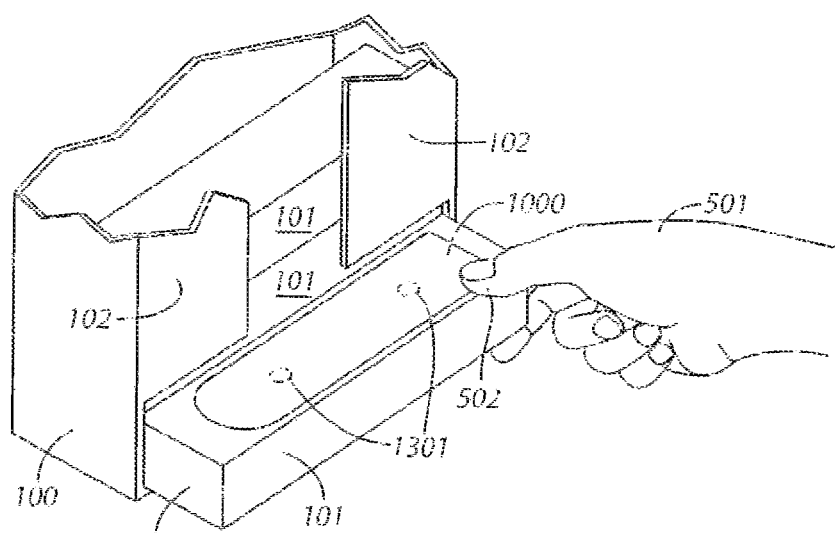
FIG. 13 comprises a perspective view as configured in accordance with various embodiments of the invention.

For example, and referring now to FIG. 13, the physically-discrete informational patient aid 1000 can be disposed between a first one of the sealed modules 101 of the plurality of sealed modules 101 that is to be removed from the housing 100 at a time of initially servicing the patient with this particular kit and a next adjacent one of the sealed modules 101 (in this case, the next highest sealed module 101 in the stack of sealed modules 101). If desired, the physically-discrete informational patient aid 1000 can be removably attached to that first one of the sealed modules 101 using one or more dabs of a tacky adhesive 1301 that will not mar or deform the physically-discrete informational patient aid 1000 and that will readily give way to permit the physically-discrete informational patient aid 1000 to be selectively removed by hand from the sealed module 101.

So configured, the physically-discrete informational patient aid 1000 can be readily removed from the housing 100 (in some cases, at the same time as the initial sealed module 101 is removed) and then handed by the medical service provider to the patient or other non-professional attendant (such as a family member). The aforementioned information on the physically-discrete informational patient aid 1000, in turn, can help to inform an anxious patient or family member about VAP in general, why the patient is to receive this oral care, and what they can do to help themselves in these regards as well. It will be appreciated that these benefits are attained with very little time requirements and/or training on the part of the medical services provider in these regards.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As one example in these regards, the physically-discrete informational patient aid 1000 can comprise the aforementioned tear-away flap 601. Upon removing the latter in order to gain access to the housed modules, the flap/bookmark can be given to the patient and/or an attending family member as desired.

We claim:

1. A prophylactic kit apparatus configured to be used by a medical services provider with only a single patient, comprising:

a plurality of sealed modules, each of the sealed modules containing at least one prophylactic agent to be used in service of the patient and wherein the sealed modules are to be used in a particular order in service of the patient;

a housing configured to contain the plurality of sealed modules such that only one of the plurality of sealed modules can be removed from the housing at a time and in the particular order, and a bookmark disposed within the housing that is physically discrete from any of the plurality of sealed modules, the bookmark having a page-engagement mechanism comprising a slot formed through the bookmark configured to temporarily capture a page of an item of reading material.

2. The prophylactic kit apparatus of claim 1 wherein the bookmark has presented thereon at least one of the following expressions:

VAP;

ventilator-associated pneumonia;

ventilator.

3. The prophylactic kit of claim 1 wherein the bookmark is loosely disposed within the housing with respect to the sealed modules.

4. The prophylactic kit of claim 1 wherein the bookmark is disposed between a first of the sealed modules to be removed from the housing at a time of servicing a patient and a next adjacent one of the sealed modules.

5. The prophylactic kit of claim 4 wherein the first of the sealed modules is disposed within the housing so as to be a first one of the sealed modules of the plurality of sealed modules to be removed from the housing at a time of initially servicing the patient.

6. The prophylactic kit of claim 5 wherein the bookmark is removably attached to the first of the sealed modules with a tacky adhesive such that the bookmark is neither marred nor deformed when removed from the first of the sealed modules in order to hand the bookmark to the patient.

7. The prophylactic kit apparatus of claim 1 wherein the slot comprises an arcuately-shaped slot.

8. The prophylactic kit apparatus of claim 1 wherein the slot is formed through the bookmark closer to one end of the bookmark than an opposing end of the bookmark.

* * * * *